United States Patent [19]

Vrouenraets

[11] Patent Number: 4,685,455
[45] Date of Patent: Aug. 11, 1987

[54] WATERVAPOR-PERMEABLE, PRESSURE SENSITIVE, ANTISEPTIC WOUND COVERING MATERIAL

[75] Inventor: Cornelius M. F. Vrouenraets, Dieren, Netherlands

[73] Assignee: Akzo nv, Arnhem, Netherlands

[21] Appl. No.: 786,484

[22] Filed: Oct. 11, 1985

[30] Foreign Application Priority Data

Oct. 16, 1984 [NL] Netherlands ........................ 8403151

[51] Int. Cl.$^4$ ............................................. A61L 15/06
[52] U.S. Cl. .................................... 128/156; 128/155; 604/307; 604/896; 604/897; 424/78; 424/447; 528/297; 528/300
[58] Field of Search .............. 128/82.1, 132 D, 132 R, 128/155, 156; 528/297, 300; 604/20, 304, 307, 892, 897, 896, 308; 424/78, 447, 448, 486

[56] References Cited

U.S. PATENT DOCUMENTS

| Re. 31,886 | 5/1985 | Hodgson | 428/40 |
|---|---|---|---|
| 3,775,374 | 11/1973 | Wolfe, Jr. | 260/75 R |
| 3,968,183 | 7/1976 | Hayashi et al. | 260/860 |
| 4,308,253 | 12/1981 | Schmid et al. | 424/54 |
| 4,310,509 | 1/1982 | Berglund et al. | 424/28 |
| 4,381,380 | 4/1983 | Le Veen et al. | 525/452 |
| 4,398,000 | 8/1983 | Kataoka et al. | 525/437 |
| 4,413,621 | 11/1983 | McCracken et al. | 128/156 |
| 4,460,369 | 7/1984 | Seymour | 604/897 |
| 4,486,488 | 12/1984 | Pietsch et al. | 428/219 |
| 4,493,870 | 1/1985 | Vrouenraets et al. | 428/245 |
| 4,513,739 | 4/1985 | Johns | 128/156 |
| 4,608,428 | 8/1986 | Shalaby et al. | 128/335.5 |

FOREIGN PATENT DOCUMENTS

| 0839556 | 4/1970 | Canada | 128/156 |
|---|---|---|---|
| 0011471 | 5/1980 | European Pat. Off. . | |
| 0024107 | 2/1981 | European Pat. Off. . | |
| 0091800 | 10/1983 | European Pat. Off. . | |
| 0107277 | 5/1984 | European Pat. Off. . | |
| 0023395 | 2/1986 | European Pat. Off. . | |
| 0178740 | 4/1986 | European Pat. Off. | 604/307 |
| 1228030 | 11/1966 | Fed. Rep. of Germany | 128/156 |
| 0038819 | 3/1982 | Japan | 528/300 |
| 0027923 | 2/1984 | Japan | 528/300 |
| 682866 | 11/1952 | United Kingdom . | |
| 1403210 | 8/1975 | United Kingdom . | |
| 1404340 | 8/1975 | United Kingdom . | |
| 0571272 | 9/1977 | U.S.S.R. | 128/132 R |

OTHER PUBLICATIONS

Kirk–Othmer, Encyclopedia of Chemical Technology, vol. 9, (1967) pp. 232–244.

*Primary Examiner*—Richard J. Apley
*Assistant Examiner*—Paul Prebilic
*Attorney, Agent, or Firm*—Stevens, Davis, Miller & Mosher

[57] ABSTRACT

Wound covering material which is impermeable to bacteria and viruses, permeable to water vapor, pressure-sensitive and antiseptic. It comprises a backing and a pressure-sensitive adhesive layer containing as a glue an acrylate ester copolymer containing hydrophilic groups and/or a mixture of polyvinylmethyl and/or polyvinylethyl ethers. The backing layer is composed of a film of a segmented copolyether ester comprising 40–85% by weight of short-chain ester units, mainly based on 1,4-butylene glycol terephthalate, and long-chain ester units derived from a glycol having a molecular weight of 800 to 6000 and an atomic ratio of carbon to oxygen between 2.0 and 4.3, provided that at least 15% by weight and not more than 40% by weight of the long-chain ester units have an atomic ratio of carbon to oxygen between 2.0 and 2.4. The backing layer contains 1 to 15% by weight of iodine or 0.1 to 8% by weight of 1,6-bis(4-chlorophenyl-diguanido)hexane (i.e. chlorhexidene), calculated on the weight of the copolyether-ester. The water vapor permeability of the backing and the adhesive layer together is at least 400 g/m$^2$/24 hours in accordance with ASTM/-E96-66 [Procedure B; measured at 30° C. and a $\Delta$RH of 50%].

7 Claims, No Drawings

WATERVAPOR-PERMEABLE, PRESSURE SENSITIVE, ANTISEPTIC WOUND COVERING MATERIAL

The invention relates to pressure sensitive, antiseptic wound covering material impermeable to bacteria and viruses, but permeable to watervapour, comprising a substrate of a synthetic polymer and a pressure sensitive adhesive layer on at least the part of the substrate to be stuck to the skin, in which adhesive layer there is incorporated as adhesive a hydrophilic groups-containing acrylate ester copolymer and/or a mixture of polyvinyl methyl ethers and/or polyvinyl ethyl ethers.

A material of the type indicated above is known from, int. al., European Patent Application No. 11 471. For the material from which the substrate is made it is preferred that use should be made of a polyurethane in a layer thickness of 30 to 75 microns. The antiseptic is incorporated into the adhesive layer. Use is preferably made then of a finely divided dispersion of the solid silver sulphadiazine.

A disadvantage to this well-known wound covering material is that not the entire surface is antiseptic, but only the part provided with a pressure sensitive adhesive layer. A further disadvantage is that for the material from which the substrate is made use is made of a polyurethane of which the water vapour permeability is not satisfactory.

The present invention provides a pressure sensitive, antiseptic wound covering material having a far higher water vapour permeability and antiseptic properties also in these places where no adhesive layer is provided.

The invention consists in that with a wound covering material of the type indicated above as known the substrate and the adhesive layer together have a water vapour permeability of at least 400 g/m$^2$/24 hours in accordance with ASTM/E96-66 [Procedure B; measured at 30° C. and a $\Delta$RH of 50%], the substrate is a film of a copolyether-ester consisting of a multiplicity of repeating intralinear short-chain and long-chain ester units which are randomly joined head to tail through ester linkages, which long-chain ester units correspond to the formula

and which short-chain ester units correspond to the formula

where G represents a divalent radical which remains after the removal of terminal hydroxyl groups from at least one long-chain glycol having a molecular weight of 800 to 6000 and an atomic ratio of carbon to oxygen of 2,0 to 4,3, R represents a divalent radical remaining after removal of carboxyl groups from at least one carboxylic acid having a molecular weight less than 300, and D represents a divalent radical remaining after removal of hydroxyl groups from at least one diol having a molecular weight less than 250, and at least 80 mole % of the dicarboxylic acid used are terephthalic acid or the ester forming equivalents thereof and at least 80 mole % of the low-molecular weight diol 1,4-butane diol or the ester forming equivalents thereof, with the sum of the mole percentages of the dicarboxylic acid which is not terephthalic acid or the ester forming equivalents thereof and of the low-molecular weight diol which is not 1,4-butanediol or the ester forming equivalent thereof not exceeding 20, and the short-chain ester units form 40–85% by weight of the copolyetherester, at least 15% by weight and not more than 40% by weight of the copolyetherester is formed by long-chain ester units in which the long-chain glycol has an atomic carbon to oxygen ratio of 2,0 to 2,4, and the copolyetherester film contains 1 to 15% by weight of iodine or 0,1 to 8% by weight of 1,6- bis(4-chlorophenyldiguanido)-hexane, calculated on the weight of the copolyetherester.

It should be added that the use of an antiseptic, viz. iodine, in a product of a synthetic polymer for medical use is known in itself from U.S. Pat. No. 4,381,380. The polymer described in it, however, is a polyurethane of which the urethane groups and the urea groups present function as an iodophor.

The use of iodine and 1,6-bis(4-chlorophenyldiguanido)hexane in wound covering material is also mentioned in the European Patent Applications 23 395 and 24 107. The antiseptic used in them, however, is exclusively contained in the adhesive layer. For the substrate preference is given to a polyethylene film. A disadvantage to an antiseptic in the adhesive layer is that it is only present in the places where an adhesive layer is applied. A further disadvantage is the far shorter diffusion towards the dressed limb, which may result in a considerable reduction of the period over which the material displays its antiseptic action.

Finally, mention should still be made of European Patent Application 91 800, which describes a water-tight, but watervapour permeable, pressure sensitive surgical dressing material. The substrate may be formed then of a copolyetherester film. Nothing is said about the composition of the copolyetherester film. Preference is given, however, to a polyurethane film. There is no question of the use in it of an antiseptic.

It must be considered particularly surprising that both iodine and 1,6-bis(4-chlorophenyldiguanido)hexane (i.e. chlorhexidine) can be readily incorporated into a copolyetherester film of the afore-mentioned composition by steeping the film for half a minute up to a few minutes in a dilute aqueous or alcoholic solution of iodine and sodium iodine or a dilute aqueous solution of a salt of 1,6-bis(4-chorophenyldiguanido)hexane. In actual practice use may be made for it of an 0,005 to 0,05N iodine solution in water or an approximately 20% by weight-solution in water of the gluconate of chlorohexidine.

The degree of water vapour permeability of the copolyether ester film is, of course, not only dependent on the composition of the film, but also on the film thickness, the composition of the adhesive layer and its thickness. At any chosen combination the watervapour permeability should always be at least 400 g/m$^2$/24 hours in accordance with ASTM E-96-66 (Procedure B; measured at 30° C. and a $\Delta$RH of 50%.

It has been found that very favourable results are obtained when the thickness of the polymer film is in the range of 10 to 55 $\mu$m and the thickness of the adhesive layer is in the range of 10 to 60 $\mu$m. Optimum results are generally obtained when the thickness of the polymer film is in the range of 20 to 30 $\mu$m and the thickness of the adhesive layer, for which preferably a mixture of polyvinylethyl ethers is used, is in the range of 25 to 50 μm. The adhesive layer may cover the entire copolyetherester film or only part of it. It is generally preferred that use be made of a wound covering material in which 30 to 70% of the copolyetherester film is covered with an adhesive layer.

Suitable adhesives for use in the wound covering material according to the invention are hydrophilic groups-containing acrylate ester copolymers and/or a mixture of polyvinylmethyl ethers and/or a mixture of polyvinylethyl ethers.

Examples of suitable adhesives based on acrylate ester copolymers are described, among other places, in European Patent Application No. 35 399.

For the preparation of the copolyetheresters to be used in the composite products according to the present invention reference is made to British Patent Specifications Nos. 682 866, 1 403 210 and 1 404 340.

Preference is given to copolyetheresters of which the short-chain ester units entirely or substantially consist of polybutylene terephthalate units. Films of these copolyetheresters are easy to prepare. Moreover, films of this material generally show better physical properties for the present use than films of copolyetheresters in which for instance 20% of the terephthalic acid has been replaced with a different dicarboxylic acid. For special uses replacement of a small percentage of the 1,4-butanediol with an other diol and/or replacement of terephthalic acid with an other low molecular weight dicarboxylic acid may be of advantage. Included among low molecular weight diols (other than 1,4-butanediol) which are converted into short-chain ester units are acyclic, alicyclic and aromatic dihydroxy compounds.

Preferred are diols with 2-15 carbon atoms such as ethylene, propylene, isobutylene, pentamethylene, 2,2-dimethyltrimethylene, hexamethylene, and decamethylene glycol, dihydroxy cyclohexane, dimethanol cyclohexane, resorcinol, hydroquinone and 1,5-dihydroxy naphthalene.

Especially preferred are aliphatic diols containing 2-8 carbon atoms. Included among the bis-phenols which can be used are bis(p-hydroxy)diphenyl, bis(p-hydroxyphenyl)methane and bis(p-hydroxyphenyl)propane.

Corresponding ester forming derivatives of diols are also suitable for use (for instance epoxy ethane or ethylene carbonate may be used instead of ethylene glycol).

The term "low molecular weight diols" as used in the description of the invention also refers to these corresponding ester forming derivatives, the molecular weight requirement relating to the diol as such and not to derivatives thereof.

Suitable dicarboxylic acids (other than terephthalic acid) which are reacted with the afore-mentioned long-chain glycols and with low molecular weight diols to form copolyesters are aliphatic, cycloaliphatic or aromatic dicarboxylic acids having a molecular weight not higher than 300. The term dicarboxylic acid used in the description of the invention also refers to equivalents of dicarboxylic acids having two functional carboxyl groups whose behaviour is practically the same as that of the dicarboxylic acids in the conversion with glycols and diols to copolyesters. These equivalents include esters and ester forming derivatives, such as the acid halides and anhydrides. The requirements regarding the molecular weight relate to the acid and not to equivalent esters or ester forming derivatives thereof. The dicarboxylic acids may contain randomly substituted groups or combinations which do not detrimentally affect polyester formation or the use of the polymer in the elastomeric compositions according to the invention. Aliphatic dicarboxylic acids, as the term is used herein, are carboxylic acids having two carboxylgroups which are each attached to a saturated carbon atom. Aliphatic or cycloaliphatic acids having conjugated unsaturation often cannot be used because of homopolymerization. However, some unsaturated acids, such as maleic acid, can be used. Aromatic dicarboxylic acids, as the term is used herein, are dicarboxylic acids having two carboxyl groups attached to a carbon atom in an isolated or fused benzene ring. It is not necessary that both functional carboxyl groups be attached to the same aromatic ring and where more than one ring is present, they can be joined by aliphatic or aromatic divalent radicals or divalent radicals such as —O— or —SO$_2$—.

Preference is given to cyclohexane dicarboxylic acids and adipic acid.

Representative aromatic dicarboxylic acids which can be used include phthalic and isophthalic acids, bibenzoic acid, substituted dicarboxy compounds with two benzene nuclei such as bis(p-carboxyphenyl)methane, p-oxy(p-carboxyphenyl)benzoic acid, ethylene-bis(p-oxybenzoic acid) 1,5-naphthalene dicarboxylic acid, 2,6-naphthalene dicarboxylic acid, 2,7-naphthalene dicarboxylic acid, phenanthrene dicarboxylic acid, anthracene dicarboxylic acid, 4,4'-sulfonyl dibenzoic acid and $C_1$–$C_{12}$ alkyl and ring substitution derivatives thereof, such as halo, alkoxy, and aryl derivatives. Hydroxyl acids such as p(β-hydroxy-ethoxy)benzoic acid can also be used providing an aromatic dicarboxylic acid is also present.

Aromatic dicarboxylic acids are a preferred class for preparing the copolyester polymers of this invention. Among the aromatic acids, those with 8-16 carbon atoms are preferred, particularly the phenylene dicarboxylic acids, i.e., phthalic and isophthalic acids.

The long-chain glycols preferably entirely consist of polyethylene oxide glycol. In some cases it may be desirable to make use of random or block copolymers of epoxyethane and minor amounts of a second epoxy alkane. It is preferred that the second monomer should form less than 40 mole % of the polyalkylene oxide glycols and, more preferably, less than 20 mole %. Examples of suitable second monomers include 1,2- and 1,3-epoxy propane, 1,2-epoxy butane and tetrahydrofuran. Alternatively, use may be made of mixtures of polyethylene oxide glycol and a second polyalkylene oxide glycol, such as poly-1,2-propylene oxide glycol or polytetramethylene oxide glycol.

The polymers described herein can be made conveniently by a conventional ester interchange reaction. A preferred procedure involves heating the dimethyl ester of terephthalic acid with a long chain glycol and a molar excess of 1,4-butanediol in the presence of a catalyst at 150° to 260° C. followed by distilling off methanol formed by the interchange. Heating is continued until methanol evolution is complete. Depending on temperature, catalyst and glycol excess, this polymerization is complete within a few minutes to a few hours. This procedure results in the preparation of a low molecular weight prepolymer which can be carried to a high molecular weight copolyester of this invention by the procedure described below. Such prepolymers can also be prepared by a number of alternate esterification or ester interchange processes; for example, the long-chain glycol can be reacted with a high or low molecular weight short-chain ester homopolymer or copolymer in the presence of catalyst until randomization occurs. The short-chain ester homopolymer or copolymer can be prepared by ester interchange from either the dimethyl esters and low molecular weight diols, as above, or from the free acids with the diol acetates. Alternatively, the short-chain ester copolymer can be prepared by direct esterification from appropriate acids, anhydrides or acid chlorides, for example, with diols or by other processes such as reaction of the acids with cyclic ethers or carbonates. Obviously the prepolymer might also be prepared by running these processes in the presence of the long-chain glycol.

The resulting prepolymer is then carried to high molecular weight by distillation of the excess of short chain diol. This process is known as "polycondensation". Additional ester interchange occurs during this distillation to increase the molecular weight and to randomize the arrangement of the copolyesters units. Best results are usually obtained if this final distillation or polycondensation is run at a pressure not higher than 130 Pa and 240°–260° C. for less than 2 hours in the presence of antioxidants such as sym- di- beta- napthyl-p-phenylenediamine and 1,3,5-trimethyl-2,4,6-tri[3,5-ditertiarybutyl-4-hydroxybenzyl]benzene.

Most practical polymerization techniques rely upon ester interchange to complete the polymerization reaction. In order to avoid excessive hold time at high temperatures with possible irreversible thermal degradation, it is advantagous to employ a catalyst for ester interchange reactions. Although a wide variety of catalysts can be used, organic titanates such as tetrabutyl titanate used alone or in combination with magnesium or calcium acetate are preferred. Complex titanates, such as $Mg[HTi(OR)_6]_2$, derived from alkali or alkaline earth metal alkoxides and titanate esters are also very effective. Inorganic titanates, such as lanthanum titanate, calcium acetate/antimony trioxide mixtures and lithium and magnesium alkoxides are representative of other catalysts which can be used.

According to the invention for the long-chain glycol having an atomic carbon to oxygen ratio in the range of 2.0 to 2,4 preferably use is made of a polyethylene oxide glycol having a molecular weight in the range of 800 to 6000.

When use is made of a polyethylene oxide glycol having a molecular weight <800, the proportion thereof to be incorporated in the copolyether ester is prohibitively high. For, a film made therefrom having a thickness of, say 35 $\mu$m and a water vapour permeability of at least 400 g/m$^2$/24 hours has been found unsuitable for use in wound covering material. Also the manufacture of wound covering material from copolyether ester films prepared by using a polyethylene oxide glycol having a molecular weight >6000 leads to unsatisfactory results in that the physical properties of the copolyetherester films are very deficient in several respects, e.g. as far as strength is concerned. Generally, a wound covering material having very good properties can be obtained when the long-chain glycol having an atomic carbon to oxygen ratio in the range of 2,0 to 2,4 is a polyethylene oxide glycol having a molecular weight in the range of 2000 to 4000.

It has been found that the most favourable results are obtained with a material prepared from a copolyetherester of which the short-chain ester units substantially consist of polybutylene terephthalate units. An optimum quality was obtained when use was made of a copolyetherester in which, when exclusively use is made of polyethylene oxide glycol of a molecular weight in the range of 2000 to 4000, the percentage short-chain ester units is in the range of 70 to 80% by weight.

The manufacture of films from the present copolyetheresters is carried out in the manner known per se from the art, as described in Kirk-Othmer, Encyclopedia of Chemical Technology 9 (1966), pp. 232–241.

The manufacture of copolyetherester films is described in U.S. Pat. No. 3,968,183.

With the method described the starting material is melt extruded into film, which is cooled at a temperature in the range of 40° to 120° C. If preference is given to very thin films of 10 to 35 $\mu$m, use may be made of the film blowing method.

Once the films have been provided with an adhesive layer and been rendered antiseptic by immersion in an iodine solution or a solution of a chlorohexidine salt, they are dried and packaged in a material impermeable to bacteria and viruses.

In this packaging material the dressing will still be sterilized by subjecting it to $\gamma$-radiation of 2 to 3 Mrad.

The invention will be further described in the following examples, which are of course not to be construed as limiting the scope of the present invention.

EXAMPLE I

Into a 200-l autoclave there were introduced 33,3 kg of dimethyl terephthalate, 21,6 kg of 1,4-butanediol and 12,5 kg of polyethylene oxide glycol having an average molecular weight of 4000. The reaction mixture was heated to 110° C., with stirring, followed by adding 500 ppm of tetrabutyl titanate, calculated on dimethyl terephthalate. Upon a further increase in temperature to 160° C. methanol distilled off, after which the pressure was slowly reduced to 100 Pa and the temperature increased to 245° C.

This polycondensation reaction, which lasted 3 to 4 hours, led to a product having a relative viscosity of 2,53 (measured at a concentration of 1 g in 100 g m-cresol at 25° C.).

In the same way as indicated above several copolyetheresters were prepared using varying amounts of the above-mentioned polyethylene oxide glycols, with the proviso that the copolyetheresters B, C and D were still subjected to polycondensation in the solid phase.

The copolyetheresters prepared had the following composition:

| Wt. % short-chain ester units | $\eta_{rel}$ |
|---|---|
| A 74,2 | 2,53 |
| B 80,1 | 3,5 |
| C 75,2 | 3,8 |
| D 69,2 | 3,6 |

EXAMPLE II

The copolyetheresters prepared in Example I were blown into films having a thickness ranging from 20 to 30 $\mu$m, after which the water vapour permeability (WVP) of the films was measured at 30° C. and 50% $\Delta$RH in accordance with procedure B of ASTM E 96-66.

The results are given in the table below.

TABLE 2

| Copolyetherester | film thickness in μm | WVP (g/m²/24 hrs) |
|---|---|---|
| B | 22 | 810 |
|   | 25 | 660 |
| C | 22 | 1200 |
|   | 24 | 1120 |
| D | 30 | 1460 |

Part of the resulting films were steeped in ethanol for 1 minute and subsequently over a period of 5 minutes, they were kept in an iodine solution containing 4 g $I_2$ and 5 g NaI in 390 g ethanol. After rinsing with ethanol and drying to the air the iodine content was determined. The results of these determinations are given in Table 3.

Another part of the films was immersed in water for 1 minute and subsequently, for 5 minutes, in a solution of 20% by weight of chlorohexidine gluconate in water. After rinsing with water and drying to the air the chlorohexidine content was determined. The results of these determinations are given in Table 3.

TABLE 3

| film of copolyether ester | $I_2$ content (wt. %) | chlorohexidine content (wt. %) |
|---|---|---|
| B | 3,8 | 2,5 |
| C | 6,2 | 2,4 |
| D | 13,5 | 2,7 |

Subsequently, an adhesive solution was applied to the films to a thickness of 100 μm, which after evaporation of the solvent resulted in an adhesive layer approximately 40 μm thick.

Two different adhesives A and B were applied. The adhesive A consisted of a mixture of 31 g of a 25%-solution of polyvinylethyl ether (K-value 103-113) in hexane, 56,3 g of a 70%-solution of polyvinylethyl ether (K-value 55-65) in petroleum ether with a boiling point between 60° and 140° C. and 38 g of petroleum ether with a boiling point between 60° C. and 140° C. Adhesive B was composed of a mixture of 44,4 g of a 50%-solution of polyvinyl methyl ether (K-value 45-55) in water, 41 g of a 50% dispersion of a polyacrylate (viscosity at 25° C. [Contraves Rheometer STV, AIII] 10-40 mPa.s) and 20 g of water.

After the solvent had been evaporated, the water vapour permeability (WVP) was measured of the films thus provided with an adhesive layer.

The results of these measurements are given in Table 4.

TABLE 4

| Copolyether ester | film thickness μm | WVP with adhesive A g/m²/24 hrs. | WVP with adhesive B g/m²/24 hrs. |
|---|---|---|---|
| B | 16 | 780 | 790 |
| C | 23 | 1060 | 1150 |
| D | 22 | 1100 | 1350 |

Finally, of the material thus manufactured the antiseptic effect was measured by leaving pieces of film on an agaragar plate inoculated with *staphylococcus aureus*. The width of the circular section around the film where there has been no growth of bacteria is a measure of the antiseptic effect of the film. The test was subsequently repeated with film sterilized by γ-radiation of 2,5 Mrad. The test results are given in Table 5.

TABLE 5

| | Width (in mm) of circular section around film | | | | |
|---|---|---|---|---|---|
| | $I_2$ + adhesive A | | chlorohexidine + adhesive A | | chlorohexidine + adhesive B |
| copoly-ether ester | before γ-ra-diation | after γ-ra-diation | before γ-ra-diation | after γ-ra-diation | before γ-radiation |
| B | <0,5 | <0,5 | 4-5 | 3-5 | 0,5-1 |
| C | 2-3 | 2 | 4-5 | 3-5 | 0,5-1 |
| D | 3 | 2-3 | 4-5 | 3-5 | 1-2 |

The results in the above table clearly show the great antiseptic action of the wound covering material of the present invention. It also appears that the antiseptic action of a film with adhesive A is distinctly greater than that of a film with adhesive B. Moreover, after sterilization by γ-radiation the antiseptic action of the wound covering material according to the invention is largely retained.

EXAMPLE III

Use being made of the procedure given in Example I, three copolyetheresters K, L and M were prepared containing varying amounts of polyethylene oxide glycol of an average molecular weight of 4000. After preparation in the melt the three copolyetheresters were subjected to polycondensation in the solid phase.

The composition and the relative viscosity (measured at a concentration of 1,0 g in 100 g m-cresol at 25° C.) of the copolyetheresters thus prepared is given in the table below.

TABLE 6

| wt. % short-chain ester units | $\eta$rel |
|---|---|
| K 79,3 | 3,47 |
| L 74.2 | 3.71 |
| M 69 | 3.90 |

EXAMPLE IV

The copolyetheresters prepared in Example III were processed into films by extrusion on a chill roll of which the temperature was kept at 115° to 120° C. After the chill roll there was still provided a heating roll (temperature 115° to 120° C.). The resulting film was wound up at a speed of 14 m/minute. The extruder had a 4-zone screw having a length/diameter ratio of 25,5. The compression ratio was 2,54 and the polymer pressure 119.10⁵ Pa. The temperatures in the 4 zones of the extruder screw were, successively, 260°, 257°, 255° and 250° C.

By varying the width of the casting slit films of different thicknesses were made from each of the copolyetheresters K,L and M. Of these films the water vapour permeability was measured both before and after applying an adhesive layer (adhesive A of Example II) of the thickness indicated and consisting of a mixture of polyvinylethyl ethers.

The results are given in the table below.

TABLE 7

| copolyether ester | film thickness μm | water vapour permeability WVP in g/m² · 24 hours | | |
|---|---|---|---|---|
| | | film | film with 25 μm adhesive layer | film with 50 μm adhesive layer |
| K | 16 | 1280 | 700 | 480 |

TABLE 7-continued

| copolyether ester | film thickness μm | water vapour permeability WVP in g/m² · 24 hours | | |
|---|---|---|---|---|
| | | film | film with 25 μm adhesive layer | film with 50 μm adhesive layer |
| | 33 | 1010 | 570 | 420 |
| | 41 | 920 | 440 | 390 |
| L | 21 | 1400 | 720 | 700 |
| | 31 | 1250 | 590 | 485 |
| | 41 | 1000 | 720 | 480 |
| M | 21 | 2030 | 1070 | 670 |
| | 30 | 1890 | 960 | 670 |
| | 39 | 1700 | 900 | 585 |
| | 55 | 1430 | 890 | 550 |

Of a frequently used wound covering material of polyurethane film 28 μm thick and provided with a polyvinylethyl ether layer 38 μm thick a WVP of 300 g/m² 24 hours was measured. This film however had no antiseptic properties.

EXAMPLE V

Copolyetheresters K, L and M prepared in accordance with the procedure of Example III were extruded into three films each having a thickness of about 30 μm.

These films were treated in the way indicated in Example II with an aqueous 0,01N $I_2$ solution or with an aqueous solution containing about 20% by weight of chorohexidine-gluconate. Finally, the films were coated with an adhesive layer of 50 μm containing an adhesive A.

The resulting films were tested for their antiseptic action in the way indicated in Example II. The results are given in the table below.

TABLE 8

| copolyether ester | wt. % chloro hexidine | width of circ. section (mm) | wt. % $I_2$ | width of circ. section (mm) |
|---|---|---|---|---|
| K | 0.3 | 0.1 | 2,34 | 0,1 |
| | 2,5 | 4-5 | 3,8 | 0,1 |
| L | 0.5 | 0.1 | 2,33 | 0,3 |
| | 2,4 | 4-5 | 6,2 | 2-3 |
| M | 0,85 | 0.1 | 4,5 | 0,3 |
| | 2,7 | 4,5 | 13,5 | 3 |

EXAMPLE VI

Use being made of the procedure given in Example I, two copolyetheresters P and Q were both prepared using two polyether glycols, viz. polyethylene oxide glycol (PEG) (average molecular weight 4000) and polytetramethylene oxide glycol (PTMG) (average molecular weight 1000). Of the dimethyl terephthalate a proportion of 15% had been replaced with dimethyl isophthalate. After preparation in the melt the two copolyetheresters were subjected to polycondensation in the solid phase. The composition and the relative viscosity (measured at a concentration of 1,0 g in 100 g of m-cresol at 25° C.) of the resulting copolyetheresters is given in the table below.

TABLE 9

| copoly-ether-ester | wt % long-chain ester units with PEG 4000 | wt % long-chain ester units with PTMG 1000 | wt % short-chain ester units |
|---|---|---|---|
| P | 25,8 | 11,3 | 62,9 |

TABLE 9-continued

| copoly-ether-ester | wt % long-chain ester units with PEG 4000 | wt % long-chain ester units with PTMG 1000 | wt % short-chain ester units |
|---|---|---|---|
| Q | 31 | 11,3 | 57,7 |

In accordance with the procedure indicated in Example IV these polymers were processed into films having a thickness of 20 μm and 30 μm. Of these films the water vapour permeability was measured both before and after applying an adhesive layer (adhesive A of Example II) of the thickness indicated and consisting of a mixture of polyvinylethyl ethers.

The results are given in the table below.

TABLE 10

| copolyether-ester | film thickness μm | water vapour permeability (WVP) in g/m²/24 hours | |
|---|---|---|---|
| | | film | 30 μm film with 50 μm adhesive layer |
| P | 20 | 1640 | 450 |
| | 30 | 1460 | |
| Q | 20 | 1930 | 600 |
| | 30 | 1840 | |

In accordance with the procedure given in Example II the two films were treated respectively with 0,01N $I_2$ solution and with a solution containing about 20% by weight of chlorhexidine gluconate in water. Finally, the films were provided with an adhesive A-containing layer to a thickness of 50 μm.

The resulting films were tested for their antiseptic action in the way indicated in Example II. The results are given in the table below.

TABLE 11

| copolyether-ester | wt % chloro-hexidine | wt % $I_2$ | width (in m) of circular section around film | |
|---|---|---|---|---|
| | | | chlorhexidine | $I_2$ |
| P | 2,05 | 5,3 | 1,5-2 | 1 |
| Q | 2.6 | 3.6 | 2 | 0.5 |

EXAMPLE VII

Use being made of the same procedure as given in Example I, two copolyetheresters R and T were prepared, the polyether being a polyethylene oxide glycol (PEG) of a molecular weight of 1000 and 2000, respectively. After polycondensation in the solid phase copolyetherester R with 66% by weight of butylene terephthalate units and 34% by weight of polyethylene oxide glycol (MW 1000)-terephthalate units had a $\eta_{rel}$ of 4,2.

After polycondensation in the solid phase copolyetherester T with 68% by weight of butylene terephthalate units and 32% by weight of polyethylene oxide glycol (MW 2000)-terephthalate units had a $\eta_{rel}$ of 5,0.

These copolyetheresters were processed into films having a thickness of 23 (copolyetherester R) and 22 μm (copolyetherester T), respectively.

The table below shows the results of the water vapour permeability measurements on the resulting films, which were provided or not with an adhesive layer having a thickness of 25 and 50 μm, respectively (Adhesive A of Example II).

TABLE 12

| copolyether-ester | film thickness in μm | WVP (g/m²/24 h) at a thickness of the adhesive layer of | | |
| --- | --- | --- | --- | --- |
| | | — | 25 μm | 50 μm |
| R | 23 | 1135 | 703 | 490 |
| T | 22 | 1410 | 820 | 560 |

What is claimed is:

1. Pressure sensitive, antiseptic wound covering material impermeable to bacteria and viruses, but permeable to watervapour, comprising a substrate of a synthetic polymer and a pressure sensitive adhesive layer on at least the part of the substrate to be stuck to the skin, in which adhesive layer there is incorporated as adhesive a hydrophilic groups-containing acrylate ester copolymer and/or a mixture of polyvinyl methyl ethers and/or polyvinylethyl ethers, characterized in that the substrate and the adhesive layer together have a water vapour permeability of at least 400 g/m²/24 hours in accordance with ASTM/E96-66 [Procedure B; measured at 30° C. and ΔRH of 50%], the substrate is a film of a copolyetherester consisting of a multiplicity of repeating intralinear long-chain and short-chain ester units which are randomly joined head to tail through ester linkages, which long-chain ester units correspond to the formula

and which short-chain ester units correspond to the formula

where G represents a divalent radical which remains after the removal of terminal hydroxyl groups from at least one long-chain glycol having a molecular weight of 800 to 6000 and an atomic ratio of carbon to oxygen of 2,0 to 4,3, R represents a divalent radical remaining after removal of carboxyl groups from at least one carboxylic acid having a molecular weight less than 300, and D represents a divalent radical remaining after removal of hydroxyl groups from at least one diol having a molecular weight less than 250, and at least 80 mole % of the dicarboxylic acid used are terephthalic acid or the ester forming equivalents thereof and at least 80 mole % of the low-molecular weight diol 1,4-butane diol or the ester forming equivalents thereof, with the sum of the mole percentages of the dicarboxylic acid which is not terephthalic acid or the ester forming equivalents thereof and of the low-molecular weight diol which is not 1,4-butanediol or the ester forming equivalent thereof not exceeding 20, and the short-chain ester units form 40–85% by weight of the copolyetherester, at least 15% by weight and not more than 40% by weight of the copolyetherester is formed by long-chain ester units in which the long-chain glycol has a carbon to oxygen ratio of 2,0 to 2,4, and the copolyether ester film contains 1 to 15% by weight of iodine or 0,1 to 8% by weight of 1,6-bis(4-chlorophenyl-diguanido)hexane (i.e. chlorhexidine), calculated on the weight of the copolyetherester.

2. Wound covering material according to claim 1, characterized in that the long-chain glycol having an atomic carbon to oxygen ratio in the range of 2,0 to 2,4 is polyethylene oxide glycol having a molecular weight in the range of 2000 to 4000.

3. Wound covering material according to claim 1, characterized in that the thickness of the polymer film is in the range of 10 to 55 μm, preferably in the range of 20 to 30 μm.

4. Wound covering material according to claim 1, characterized in that the short-chain ester units consist of polybutylene terephthalate units.

5. Wound covering material according to claim 1, characterized in that use is made of polyethylene oxide glycol of a molecular weight in the range of 2000 to 4000 and the amount of the short-chain ester units in the copolyetherester is in the range of 70 to 80% by weight.

6. Wound covering material according to claim 1, characterized in that the thickness of the pressure sensitive adhesive layer is in the range of 10 to 60 μm.

7. Wound covering material according to claim 1, characterized in that it is contained in a packaging material impermeable to bacteria and viruses and is sterilized by γ-radiation.

* * * * *